(12) United States Patent
Chen et al.

(10) Patent No.: US 11,008,322 B1
(45) Date of Patent: May 18, 2021

(54) METHOD OF SYNTHESIZING (1S,12BS) LACTAM ESTER COMPOUND

(71) Applicant: Sichuan University, Sichuan (CN)

(72) Inventors: Fener Chen, Sichuan (CN); Pei Tang, Sichuan (CN); Wen Zhang, Sichuan (CN); Lin Dong, Sichuan (CN); Youcai Xiao, Sichuan (CN)

(73) Assignee: Sichuan University, Chengdu (CN)

( * ) Notice: Subject to any disclaimer, the term of this patent is extended or adjusted under 35 U.S.C. 154(b) by 0 days.

(21) Appl. No.: 16/842,744

(22) Filed: Apr. 7, 2020

(30) Foreign Application Priority Data

Feb. 19, 2020 (CN) .................. 2020101023903.9

(51) Int. Cl.
*C07D 471/14* (2006.01)
(52) U.S. Cl.
CPC .................. *C07D 471/14* (2013.01)
(58) Field of Classification Search
None
See application file for complete search history.

(56) References Cited

FOREIGN PATENT DOCUMENTS

| CN | 1972904 A | 5/2007 |
|----|-----------|--------|
| CN | 102102114 A | 6/2011 |
| CN | 102453017 A | 5/2012 |
| CN | 108084129 A | 5/2018 |

OTHER PUBLICATIONS

Laine et al. Molecules, vol. 19, pp. 1544-1567 (Year: 2014).*
de Silva et al, Organic Letters, vol. 11, No. 15, pp. 3238-3241 (Year: 2009).*
Zhang et al, Chemistry—A European Journal, 26, 10439-10443 (Jul. 20, 2020).*

* cited by examiner

*Primary Examiner* — Zinna Northington Davis

(57) ABSTRACT

Disclosed herein is a method of synthesizing a (1S,12bS) lactam ester compound, including: subjecting a dihydrocarboline diester compound of formula (II) to asymmetric hydrogenation and lactamization in an organic solvent in the presence of an iridium catalyst precursor, a chiral diphosphine ligand and a halogen-containing reagent under hydrogen atmosphere to produce the (1S,12bS) lactam ester compound of formula (I), as shown in the following reaction scheme, where $R^1$, $R^2$ and $R^3$ are defined in the same manner with the specification.

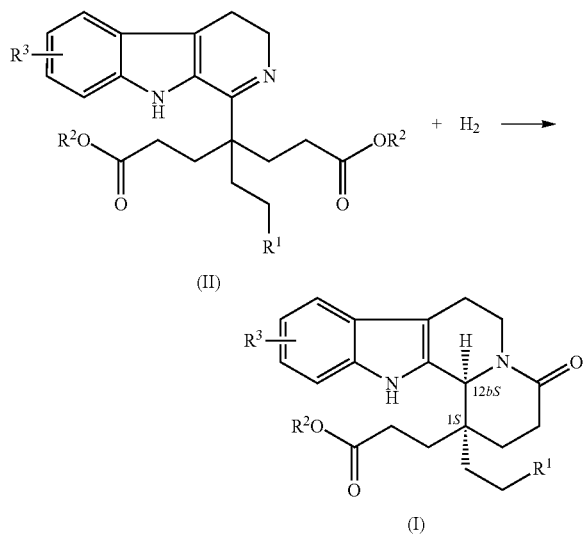

10 Claims, No Drawings

METHOD OF SYNTHESIZING (1S,12BS) LACTAM ESTER COMPOUND

CROSS-REFERENCE TO RELATED APPLICATIONS

This application claims the benefit of priority from Chinese Patent Application No. 202010102390.9, filed on Feb. 19, 2020. The content of the aforementioned application, including any intervening amendments thereto, is incorporated herein in its entirety by reference.

TECHNICAL FIELD

This application related to organic synthesis, and more particularly to a method of synthesizing a (1S,12bS) lactam ester compound (I).

BACKGROUND

Vincamine alkaloids show various pharmacological effects on cell proliferation, cardiovascular system and brain functions, especially on the cerebral vasodilation and neuroprotection. They display antioxidative and anti-cancer activities, and allow for improved circulation and cognitive ability, neuroprotection and boosted intelligence. During the preparation of the vincamine alkaloids, a (1S,12bS) lactam ester compound (I) is considered to be a vital intermediate.

Kuehne et al. (J. Am. Chem. Soc. 1964, 86, 2946) first reported a method of preparing a raceme of compound (I) (the cis-trans ratio was not specified; $R^1=R^3=H$, $R^2=Me$) by subjecting tryptamine and dimethyl 4-ethyl-4-formylpimelate to Pictet-Spengler reaction followed by lactamization. Ho et al. (Helv. Chim. Acta. 2006, 89, 249) disclosed another method of preparing a raceme of compound (I) (cis/trans=1:1.3; $R^1=R^3=H$, $R^2=H$, Et, Bn or SePh), where 1-(1-tert-butyl)-1-(1-ethylcyclohept-4-en-1-yl)-3,4-dihydro-1H-pyrido[3,4-b]indole-2, 9-dicarboxylate was oxidized by potassium permanganate under phase transfer conditions, and the resulting product was then treated with p-toluenesulfonic acid to remove the t-butoxycarbonyl group and could be converted to the racemic compound (I) via lactamization. Nemes et al. (ARKIVOC, 2008, 3, 154) prepared a raceme of compound (I) (cis/trans=2:3; $R^1=R^3=H$, $R^2=Me$) using the method reported by Kuehne, which was then sequentially hydrolyzed in a solution of sodium hydroxide in methanol, acidified by concentrated hydrochloric acid, resolved with (−)-ephedrine as a resolving agent and subjected to methyl esterification to produce methyl 3-[(1S,12bR)-1-ethyl-1,2,3,4,6,7,12,12b-octahydro-4-oxoindolo[2,3-a] quinazin-1-yl] propionate. However, such resolving agent has been under strict management and control and has not been readily available since it can be used in the preparation of narcotic drugs, and this method only has a resolution rate of 26%.

In the above methods, the products obtained are dominated by trans conformation. Two literatures only involve the preparation of raceme, and the other one has the defects of low resolution efficiency, complicated operation and high cost, so it is not suitable for the development and production of related drugs. Currently, efficient preparation of cis-(1S,12bS) lactam ester compound (I) remains a challenge in the art.

Therefore, it is of great significance to develop a method for preparing a cis-(1S,12bS) lactam ester compound (I) with simple process, low cost and environmental friendliness.

SUMMARY

An object of the invention is to provide a method of asymmetrically synthesizing (1S,12bS) lactam ester compound (I) with simple process, high efficiency, low cost and environmental friendliness to overcome the defects in the prior art, where the (1S,12bS) lactam ester compound (I) is an important intermediate in the synthesis of vincamine alkaloids.

The technical solutions of the invention are described as follows.

The invention provides a method of synthesizing a (1S,12bS) lactam ester compound of formula (I)

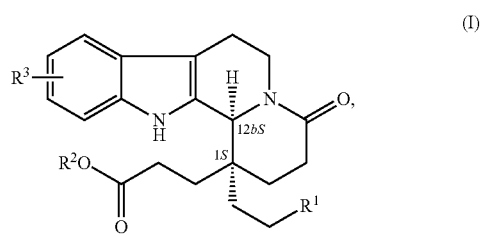

comprising:

subjecting a dihydrocarboline diester compound of formula (II) to asymmetric hydrogenation and lactamization in an organic solvent in the presence of an iridium catalyst precursor, a chiral diphosphine ligand and a halogen-containing reagent under hydrogen atmosphere to produce the (1S,12bS) lactam ester compound (I), as shown in the following reaction scheme:

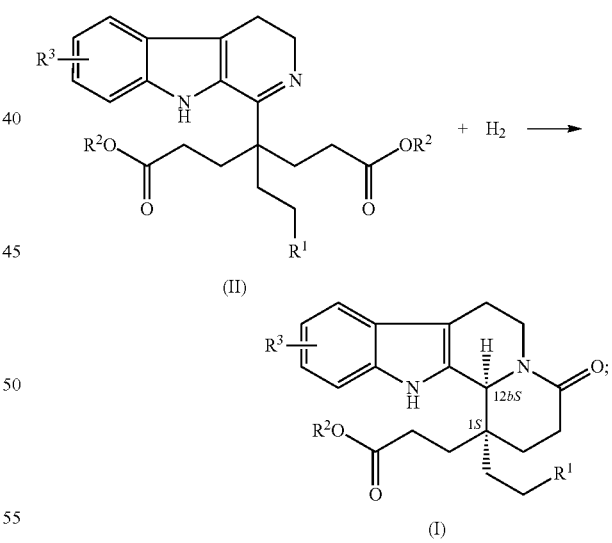

wherein:

$R^1$ is hydrogen, linear $C_1$-$C_5$ alkyl ether group, branched $C_1$-$C_5$ alkyl ether group, allyl ether group, benzyl ether group, methyl silyl ether group, isopropyl silyl ether group, tert-butyl silyl ether group or phenylsilyl ether group;

$R^2$ is linear or branched $C_1$-$C_5$ alkyl, aralkyl or aryl; and $R^3$ is hydrogen, linear or branched $C_1$-$C_5$ alkyl, linear or branched $C_1$-$C_3$ alkoxy or halogen.

In an embodiment, $R^1$ is hydrogen or linear or branched $C_1$-$C_5$ alkyl ether group; $R^2$ is linear or branched $C_1$-$C_5$ alkyl; and R³ is hydrogen or linear or branched C₁-C₅ alkyl. The substitution of R³ may occur at any substitutable position on the benzene ring.

After the reaction is completed, the reaction mixture may be subjected to post-treatment to produce the desired compound, for example, after the hydrogen is slowly released, the solvent is removed, and then the reaction mixture is separated using a silica gel column to produce the desire compound.

The method of the invention can prepare the (1S,12bS) lactam ester compound with a yield greater than 90%, dr (cis/trans) greater than 1.8:1 (up to 17:1), cis-products have higher than 88% ee (even higher than 99% ee after recrystallization) and trans-products have higher than 78% ee (even higher than 99% ee after recrystallization).

In an embodiment, the iridium catalyst precursor is selected from the group consisting of di-mu-methoxobis(1,5-cyclooctadiene)diiridium(I), chloro(1,5-cyclooctadiene) iridium(I) dimer, bis(cyclooctene)iridium(I) chloride dimer, bis(1,5-cyclooctadiene)iridium(I)tetrakis[3,5-bis(trifluoromethyl)phenyl]borate, 1,5-cyclooctadiene(pyridine)(tricyclohexylphosphine)iridium(I) hexafluorophosphate, bis(1,5-cyclooctadiene)iridium(I) tetrafluoroborate, dicholo (pentamethylcyclopentadienyl)iridium(III) dimer, 1,5-cyclooctadiene(hexafluoroacetylacetonato)iridium(I), chloro(1,5-cyclooctadiene)(1,10-phenanthroline)iridium(I), (methylcyclopentadienyl)(1,5-cyclooctadiene)iridium(I), (tricyclohexylphosphine)(1,5-cyclooctadiene)(pyridine) iridium(I) hexafluorophosphate, carbonylchloro bis(triphenylphosphine)iridium(I), (1,5-cyclooctadiene)(acetylacetonato)iridium(I), 1,5-cyclooctadiene(H5-indenyl)iridium(I), 1-(ethylcyclopentadienyl)-1,3-(cyclohexadienyl)iridium(I), (1,5-cyclooctadiene)bis(methyldiphenylphosphine)iridium (I) hexafluorophosphate, tris(norbornadiene)(acetylacetonato)iridium(III) and a combination thereof, preferably chloro (1,5-cyclooctadiene)iridium(I) dimer.

In an embodiment, the chiral diphosphine ligand is ferrocenyl diphosphine ligand, biaryl diphosphine ligand or an enantiomer thereof, preferably 1,1'-Bis{(S)-4,5-dihydro-3H-binaphtho[1,2-c:2',1'-e]phosphino}ferrocene (also referred to as (S,S)-f-Binaphane).

In an embodiment, the halogen-containing reagent is a halogen element, an aqueous solution of hydrogen halide, a halide salt or a combination thereof.

In an embodiment, the halogen element is bromine or iodine; the aqueous solution of hydrogen halide has a molar concentration of 2.0-10.0 mol/L, preferably 3.0-6.0 mol/L, such as 5.3 mol/L; the aqueous solution of hydrogen halide is an aqueous solution of hydrogen iodide or an aqueous solution of hydrogen bromide, preferably the aqueous solution of hydrogen iodide; and the halide salt is potassium bromide, potassium iodide, sodium bromide or sodium iodide, preferably potassium iodide or sodium iodide.

In an embodiment, a molar ratio of the dihydrocarboline diester compound of formula (II) to the iridium catalyst precursor to the chiral diphosphine ligand to halogen anions in the halogen-containing reagent is 1:0.01-0.05:0.02-0.1: 0.1-0.5, preferably 1:0.01-0.03:0.02-0.06:0.1-0.5.

In an embodiment, in the asymmetric hydrogenation and lactamization, a hydrogen pressure is 20-100 atm, preferably 40-80 atm; a reaction temperature is −40° C.-40° C., preferably −40° C.-0° C., and more preferably −20° C.-0° C.; and a reaction time is 48-200 h, preferably 100-150 h.

In an embodiment, the organic solvent is a polar aprotic organic solvent, an apolar aprotic organic solvent or a combination thereof, where the polar aprotic organic solvent is selected from the group consisting of dimethylsulfoxide, N,N-dimethylformamide, ethyl acetate, acetone, DMI and a combination thereof; and the apolar aprotic organic solvent is selected from the group consisting of n-hexane, cyclohexane, petroleum ether, toluene, carbon tetrachloride and carbon disulfide. In an embodiment, the organic solvent is N,N-dimethylformamide, ethyl acetate, toluene or a combination thereof, preferably a mixture of N,N-dimethylformamide and ethyl acetate in a volume ratio of 1:1, toluene or a combination thereof.

In the present invention, the amount of the organic solvent is not particularly limited and can be determined according to actual conditions. Preferably, the organic solvent is degassed before use.

In an embodiment, the halogen-containing reagent is a single halogen-containing reagent, and the method further comprises:

(1) dispersing the iridium metal catalyst precursor and the chiral diphosphine ligand in the organic solvent; and subjecting the reaction mixture to standing or stirring at room temperature for 10-30 min;

(2) adding dihydrocarboline diester compound of formula (II) and the halogen-containing reagent to the reaction mixture obtained in step (1); and (3) transferring the reaction mixture obtained in step (2) to a high-pressure reactor; and subjecting the reaction mixture to the asymmetric hydrogenation and lactamization under hydrogen atmosphere.

In an embodiment, the halogen-containing reagent is a single halogen-containing reagent, and the method further comprises:

(1) dispersing the iridium metal catalyst precursor and the chiral diphosphine ligand in a part of the organic solvent; and subjecting the reaction mixture to standing or stirring at room temperature for 10-30 min;

(2) adding dihydrocarboline diester compound of formula (II), the halogen-containing reagent and the rest of the organic solvent to the reaction mixture obtained in step (1); and (3) transferring the reaction mixture obtained in step (2) to a high-pressure reactor; and subjecting the reaction mixture to the asymmetric hydrogenation and lactamization under hydrogen atmosphere.

In an embodiment, the halogen-containing reagent is a combination of a first halogen-containing reagent and a second halogen-containing reagent, and the method further comprises:

(1) dispersing the iridium metal catalyst precursor and the chiral diphosphine ligand in the organic solvent; adding the first halogen-containing reagent; and reacting the reaction mixture at room temperature under stirring for 5-20 h to produce a halogen-bridged iridium complex solution;

(2) adding the dihydrocarboline diester compound of formula (II) and the second halogen-containing reagent to the reaction mixture; and (3) transferring the reaction mixture to a high-pressure reactor; and subjecting the reaction mixture to the asymmetric hydrogenation and lactamization under hydrogen atmosphere.

In an embodiment, the halogen-containing reagent is a combination of a first halogen-containing reagent and a second halogen-containing reagent, and the method further comprises:

(1) dispersing the iridium metal catalyst precursor and the chiral diphosphine ligand in the organic solvent in an inert gas; adding the first halogen-containing reagent; and reacting the reaction mixture at room temperature under stirring for 5-20 h to produce a halogen-bridged iridium complex solution;

(2) subjecting the halogen-bridged iridium complex solution obtained in step (1) to separation and purification; and drying the purified product;

(3) dissolving the dried product obtained in step (2) in an organic solvent which is the same as or different from the organic solvent used in step (1); and adding the dihydrocarboline diester compound of formula (II) and the second halogen-containing reagent to the reaction mixture; and (4) transferring the reaction mixture to a high-pressure reactor; and subjecting the reaction mixture to the asymmetric hydrogenation and lactamization under hydrogen atmosphere.

In an embodiment, a molar ratio of halogen anions in the first halogen-containing reagent to halogen anions in the second halogen-containing reagent is 0.2-2:1.

In an embodiment, the first halogen-containing reagent is an aqueous solution of hydrogen halide, preferably an aqueous solution of hydrogen iodide or hydrogen bromide, and more preferably an aqueous solution of hydrogen iodide; and the second halogen-containing reagent is a halide salt, preferably potassium bromide, potassium iodide, sodium bromide or sodium iodide, and more preferably potassium iodide or sodium iodide.

In an embodiment, the aqueous solution of hydrogen halide has a molar concentration of 2.0-10.0 mol/L, preferably 3.0-6.0 mol/L, such as 5.3 mol/L.

Compared to the prior art, the method provided herein has the advantages of mild conditions, simple operation, high yield and optical purity and excellent diastereoselectivity, and thus it is suitable for the scale-up applications.

DETAILED DESCRIPTION OF EMBODIMENTS

As used herein, term "halogen-containing reagent" refers to a single or mixed halogen-containing reagent. When a single halogen-containing reagent is used, the number of moles of halogen anions in the halogen-containing reagent is the number of moles of halogen anions in the single halogen-containing reagent; and when a mixed halogen-containing reagent is used, the number of moles of halogen anions in the halogen-containing reagent is the sum of the number of moles of halogen anions in respective halogen-containing reagents.

As used herein, term "alkyl" refers to a $C_1$-$C_{50}$ alkyl, preferably a $C_1$-$C_{10}$ alkyl, and more preferably a $C_1$-$C_5$ linear or branched alkyl, such as methyl, ethyl, n-propyl, iso-propyl, n-butyl, iso-butyl, sec-butyl, t-butyl, n-pentyl and n-hexyl; a $C_1$-$C_{10}$ halogenated alkyl, preferably a $C_1$-$C_5$ linear or branched halogenatedalkyl, such as trifluoromethyl, trifluoroethyl and hexafluoroisopropyl; or a $C_3$-$C_{30}$ monocyclic, polycyclic or fused-ring alkyl, preferably a $C_3$-$C_{10}$ monocyclic, polycyclic or fused-ring alkyl, such as cyclopropyl, cyclobutyl, cyclopentyl and cyclohexyl.

As used herein, term "aryl" refers to a $C_6$-$C_{36}$ monocyclic, polycyclic or fused-ring aryl, preferably a $C_6$-$C_{14}$ monocyclic, polycyclic or fused-ring aryl, such as phenyl, naphthyl, anthryl, phenanthryl, biphenyl and binaphthyl.

As used herein, term "aralkyl" refers to an alkyl substituted with at least one aryl and preferably indicates a $C_7$-$C_{15}$ aralkyl, such as benzyl, 1-phenethyl, 2-phenylethyl, 1-phenylpropyl and 3-naphthylpropyl.

As used herein, term "alkoxy" may refer to an unprotected hydroxyl or an alkoxy formed by a linear or branched alkyl having 1-20 carbon atoms, preferably 1-10 carbon atoms, and more preferably 1-5 carbon atoms, such as methoxy, ethoxy, n-propoxy, iso-propoxy, n-butoxy, iso-butoxy, sec-butoxy and tert-butoxy.

As used herein, term "aryloxy" refers to an aryloxy formed by a monocyclic, polycyclic or fused ring aryl having 6-36 carbon atoms, preferably 6-14 carbon atoms, such as phenoxy, tolyloxy, dimethylphenoxy and naphthyloxy.

As used herein, term "halogen" refers to fluorine, chlorine, bromine or iodine.

As used herein, term "heterocyclic group" refers to an aliphatic or aromatic heterocyclic group, where the aliphatic heterocyclic group refers to a 3- to 8-membered, preferably 4- to 6-membered, monocyclic, polycyclic or fused ring aliphatic heterocyclic group having 2-14 carbon atoms and at least one heteroatom, preferably 1-3 heteroatoms such as nitrogen, oxygen and/or sulfur atoms, for example, the aliphatic heterocyclic group may be azetidinyl, azepanyl, pyrrolidinyl, piperidinyl, tetrahydrofuranyl, tetrahydropyranyl and tetrahydrothienyl; the aromatic heterocyclic group refers to a 5- or 6-membered monocyclic, polycyclic or fused ring aliphatic heterocyclic group having 2-15 carbon atoms and at least one heteroatom, preferably 1-3 heteroatoms such as nitrogen, oxygen and/or sulfur atoms, such as furyl, thienyl, pyridyl, pyrimidinyl, pyrazinyl, pyridazinyl, pyrazolyl, imidazolyl, oxazolyl, thiazolyl, benzofuranyl, benzothienyl, quinolyl, isoquinolyl and quinoxalinyl.

As used herein, term "substituted amino" refers to an amino group in which the two hydrogen atoms are independently substituted with alkyl, aryl, aralkyl, alkoxy, aryloxy and aryloxyalkyl, such as dialkylamino groups including N,N-dimethylamino, N,N-diethylamino and N,N-diisopropylamino, bicycloalkylamino groups including N,N-dicyclohexylamino, diarylamino groups including N,N-diphenylamino and N-naphthyl-N-phenylamino, and diarylalkylamino including N,N-dibenzylamino.

The chiral diphosphine ligand used herein may be a ferrocenyl diphosphine ligand or an enantiomer thereof, where the ferrocenyl diphosphine ligand has a structure of formula (1), (2), (3) or (4):

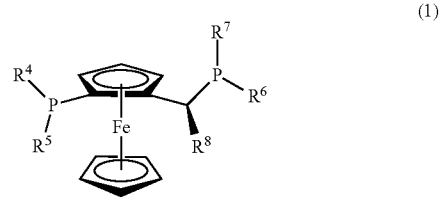

(1)

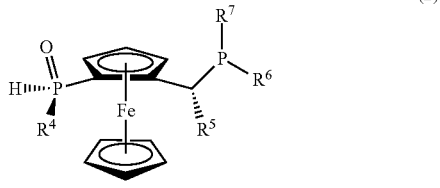

(2)

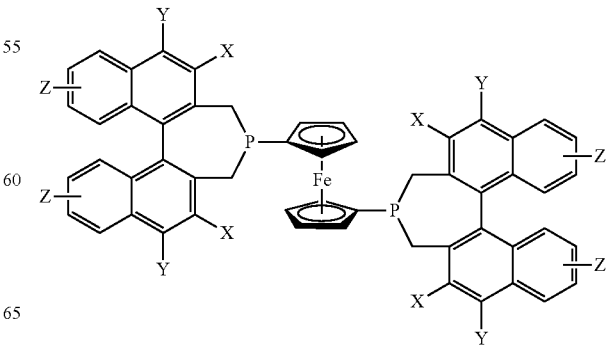

(3)

(4)

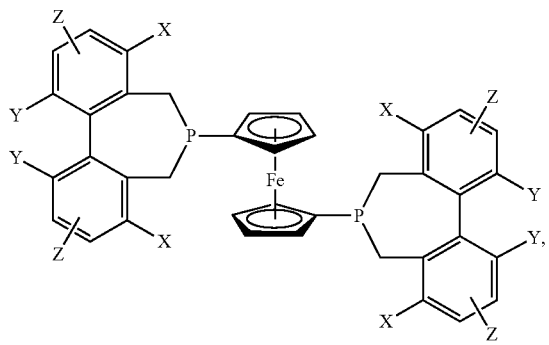

where:

in the formula (1), $R^4$ and $R^5$ are independently selected from the group consisting of alkyl, aryl, aralkyl, alkoxy, aryloxy, arylalkoxy, heterocyclyl and substituted amino; or $R^4$ and $R^5$ are linked together to form a ring; or P, $R^4$ and $R^5$ are linked together to form a group of formula (5), (6) or (7)

(5)

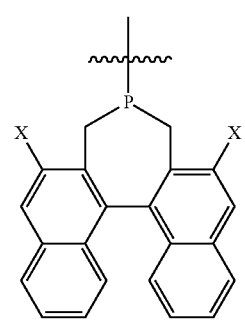

(6)

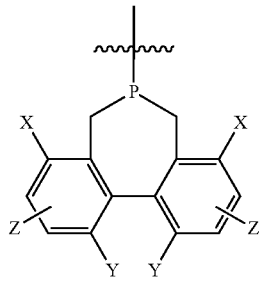

(7)

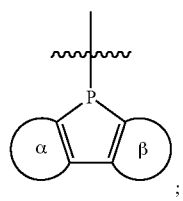

;

in the formulas (5) and (6), X is each independently hydrogen, halogen, alkyl, aryl, alkylaryl, aralkyl, alkoxy, silyl, carboxyl, ester group or amide group; Y is each independently hydrogen, halogen, alkyl, aryl, alkylaryl, aralkyl, alkoxy, silyl, carboxyl, an ester group, an amide group or a heterocyclic group; Z is each independently hydrogen, halogen, alkyl, aryl, alkylaryl, aralkyl, alkoxy, silyl, carboxyl, an ester group, an amide group or a heterocyclic group;

in the formula (7), α and β are independently substituted or unsubstituted aromatic ring;

$R^6$ and $R^7$ are independently alkyl, aryl, aralkyl, alkoxy, aryloxy, arylalkoxy, heterocyclyl or substituted amino; or $R^6$ and $R^7$ are linked together to form a ring; or P, $R^6$ and $R^7$ are linked together to form a group of formula (5), (6) or (7);

$R^8$ is alkyl, aryl, aralkyl, alkoxy, aryloxy, arylalkoxy, heterocyclyl or substituted amino;

the above groups are chiral or achiral;

in the formula (2), $R^4$ is alkyl, aryl, aralkyl, alkoxy, aryloxy, arylalkoxy, heterocyclyl or substituted amino;

$R^5$ is alkyl, aryl, aralkyl, alkoxy, aryloxy, arylalkoxy, heterocyclyl or substituted amino;

$R^6$ and $R^7$ are independently alkyl, aryl, aralkyl, alkoxy, aryloxy, arylalkoxy, heterocyclyl or substituted amino; or $R^6$ and $R^7$ are linked together to form a ring; or P, $R^6$ and $R^7$ are linked together to form a group of formula (5), (6) or (7);

the above groups are chiral or achiral;

in the formulas (3) and (4), X is each independently hydrogen, halogen, alkyl, aryl, alkylaryl, aralkyl, alkoxy, silyl, carboxyl, an ester group or an amide group; Y is each independently hydrogen, halogen, alkyl, aryl, alkylaryl, aralkyl, alkoxy, silyl, carboxyl, an ester group, an amide group or a heterocyclic group; Z is each independently hydrogen, halogen, alkyl, aryl, alkylaryl, aralkyl, alkoxy, silyl, carboxyl, an ester group, an amide group or a heterocyclic group; and the above groups are chiral or achiral.

The chiral diphosphine ligand used herein may be a biaryl diphosphine ligand or an enantiomer thereof, where the biaryl diphosphine ligand has a structure of formula (8) or (9):

(8)

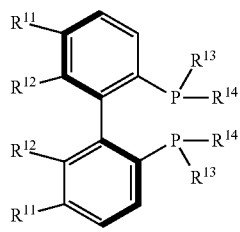

(9)

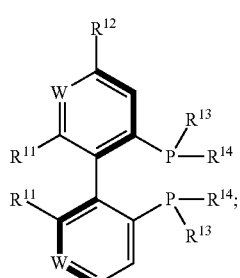

in the formula (8), $R^{11}$ and $R^{12}$ are each independently selected from the group consisting of alkyl, aryl, aralkyl, alkoxy, aryloxy, arylalkoxy, heterocyclyl and substituted amino; or $R^{11}$ and $R^{12}$ are linked together to form a ring;

$R^{13}$ and $R^{14}$ are each independently alkyl, aryl, aralkyl, alkoxy, aryloxy, arylalkoxy, heterocyclyl or substituted amino; or $R^{13}$ and $R^{14}$ are linked together to form a ring; or P, R[13] and R[14] are linked together to form a group of formula (5), (6) or (7)

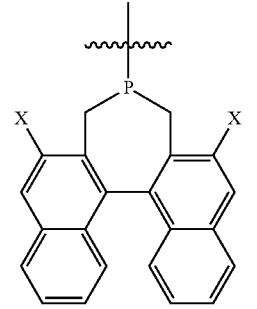

(5)

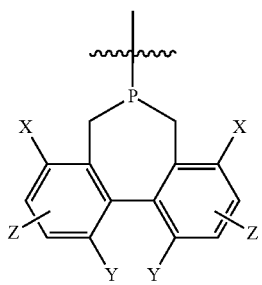

(6)

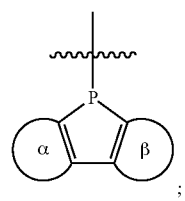

(7)

in the formulas (5) and (6), X is each independently hydrogen, halogen, alkyl, aryl, alkylaryl, aralkyl, alkoxy, silyl, carboxyl, an ester group or an amide group; Y is each independently hydrogen, halogen, alkyl, aryl, alkylaryl, aralkyl, alkoxy, silyl, carboxyl, an ester group, an amide group or a heterocyclic group; Z is each independently hydrogen, halogen, alkyl, aryl, alkylaryl, aralkyl, alkoxy, silyl, carboxyl, an ester group, an amide group or a heterocyclic group;

in the formula (7), α and β are independently substituted or unsubstituted aromatic ring; and W is each independently a nitrogen or carbon atom.

In an embodiment, the ferrocenyl diphosphine ligand used herein is selected from the group consisting of:

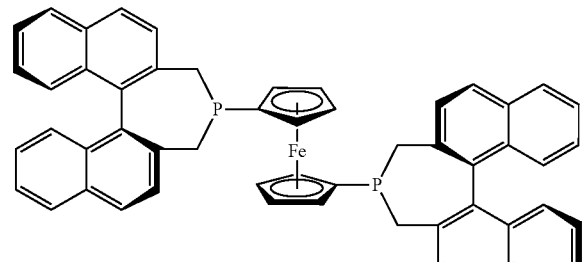

(S,S)-f-Binaphane

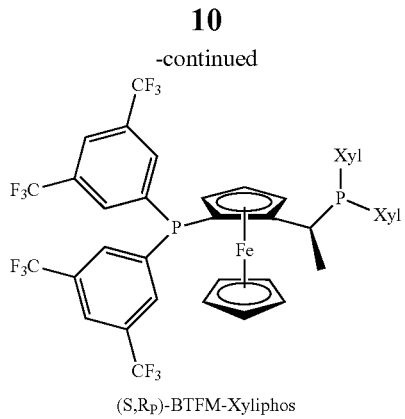

(S,R$_P$)-BTFM-Xyliphos

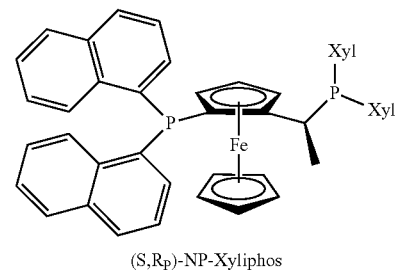

(S,R$_P$)-NP-Xyliphos

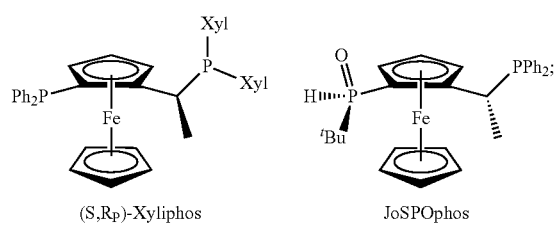

(S,R$_P$)-Xyliphos                JoSPOphos preferably (S,S)-f-Binaphane, which shows excellent enantioselectivity in the asymmetric hydrogenation and lactamation.

In an embodiment, the chiral biaryl diphosphine ligand is selected from the group consisting of:

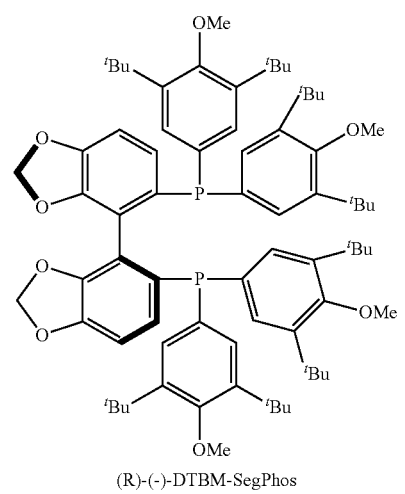

(R)-(-)-DTBM-SegPhos

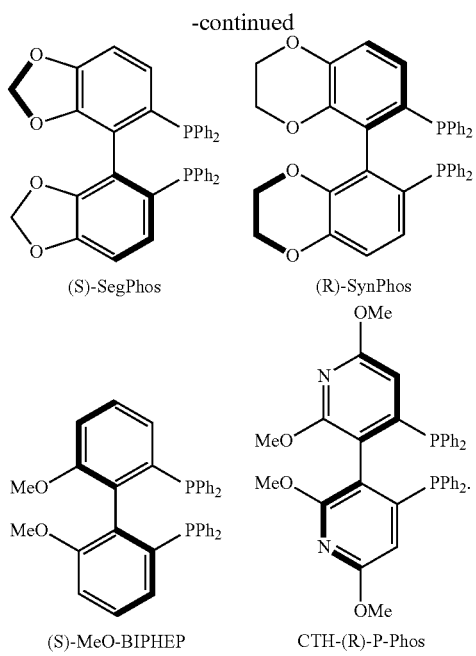

The halogen-containing reagent used herein may be a halogen element, an aqueous solution of hydrogen halide, a halide salt or a combination thereof, where the halogen element is bromine or iodine, preferably iodine; the aqueous solution of hydrogen halide is an aqueous solution of hydrogen bromide or an aqueous solution of hydrogen iodide, preferably the aqueous solution of hydrogen iodide; the aqueous solution of hydrogen halide preferably has a concentration of 2.0-10.0 mol/L, such as 5.3 mol/L; the halide salt is selected from the group consisting of lithium fluoride, sodium fluoride, potassium fluoride, rubidium fluoride, cesium fluoride, magnesium fluoride, lithium chloride, sodium chloride, potassium chloride, rubidium chloride, cesium chloride, magnesium chloride, calcium chloride, barium chloride, aluminum chloride, lithium bromide, bromide sodium, potassium bromide, rubidium bromide, cesium bromide, magnesium bromide, calcium bromide, barium bromide, aluminum bromide, lithium iodide, sodium iodide, potassium iodide, rubidium iodide, cesium iodide, magnesium iodide, calcium iodide, barium iodide and aluminum iodide, preferably potassium bromide, potassium iodide, sodium bromide or sodium iodide, and more preferably potassium iodide or sodium iodide.

The organic solvent used herein is a polar aprotic organic solvent, an apolar aprotic organic solvent or a protic organic solvent, where the polar aprotic organic solvent is selected from the group consisting of methyl formate, ethyl formate, n-propyl formate, iso-propyl formate, t-butyl formate, methyl acetate, ethyl acetate, n-propyl acetate, iso-propyl acetate, t-butyl acetate, ethyl acetoacetate, methyl propionate, ethyl propionate, methyl benzoate, ethyl benzoate, dimethyl carbonate, ethyl pyruvate, diethyl malonate, tert-butyl bromacetate, N,N-dimethylformamide, N,N-dimethylacetamide, 1,3-dimethyl-2-imidazolinone, dimethyl sulfoxide, acetone, DMI, acetonitrile and a combination thereof, preferably N,N-dimethylformamide, ethyl acetate or a combination thereof, and more preferably a mixture of N,N-dimethylformamide and ethyl acetate in a volume ratio of 1:1; the apolar aprotic organic solvent is selected from the group consisting of benzene, toluene, xylene (o-xylene, m-xylene and p-xylene), mesitylene, chlorobenzene, fluorobenzene, n-hexane, cyclohexane, n-heptane, n-pentane, diethyl ether, petroleum ether, tetrahydrofuran, methyltetrahydrofuran, dioxane, methyl tert-butyl ether, diisopropyl ether, ethylene glycol dimethyl ether, 1,2-dimethoxybenzene, dichloromethane, 1,2-dichloroethane, carbon tetrachloride and carbon disulfide, preferably toluene; and the protic organic solvent is selected from the group consisting of methanol, ethanol, isopropanol, butanol, cyclopentanol, trifluoroethanol, 1,2-propanediol, 1,3-propanediol, benzyl alcohol, phenylethanol, 1-phenylpropanol, 2-phenylpropanol, 3-phenylpropanol, formic acid, acetic acid, propionic acid, benzoic acid, 3-phenylpropionic acid, aniline, triethanolamine, 1,2-propanediamine, diethylamine, triethylamine and ethylenediamine.

The invention will be described in detail below with reference to the embodiments, and these embodiments are not intended to limit the invention.

Example 1 Preparation of methyl 3-[(1S,12bS)-1-ethyl-1,2,3,4,6,7,12,12b-octahydro-4-oxoindolo[2,3-a]quinolizin-1-yl]propionate (Ia)

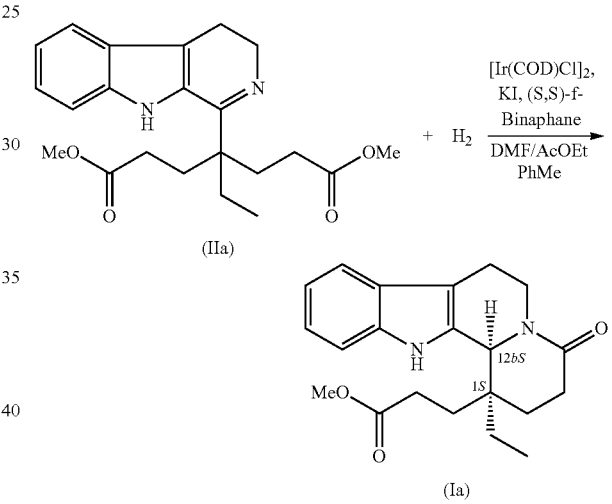

A mixture of N,N-dimethylformamide and ethyl acetate (v/v=1:1) was used herein as a solvent. 0.020 g of chloro(1,5-cyclooctadiene)iridium(I) dimer (0.030 mol) and 0.050 g of (S,S)-f-Binaphane (0.063 mmol) were dissolved in 50 mL of a degassed mixture of N,N-dimethylformamide and ethyl acetate (v/v=1:1) in a dry flask. The reaction mixture was allowed to stand for 15 min, added with 50 mL of the degassed mixture of N,N-dimethylformamide and ethyl acetate (v/v=1:1) containing 1.150 g of dimethyl 4-(4,9-dihydro-3H-pyrido[3,4-b]indol-1-yl)-4-ethylpimelate (IIa) (3.000 mmol) and 0.050 g of potassium iodide (0.300 mmol) and then transferred to a high-pressure reactor. The high-pressure reactor was subjected to hydrogen substitution three times and then introduced with hydrogen to 60 atm. The reaction mixture was stirred at −20° C. for 100 h, and then the hydrogen was slowly discharged. The reaction mixture was evaporated to remove the solvent and separated by silica gel column to give 0.960 g of a white powder product (Ia) (90% yield, dr(cis/trans)=1.8:1, cis: 91% ee and greater than 99% after recrystallization, trans: 91% ee and greater than 99% after recrystallization) with $[\alpha]^{25}_D$ of −140.2 (c1.0, MeOH).

Toluene was used herein as a solvent. In a dry flask, 0.020 g of chloro(1,5-cyclooctadiene)iridium(I) dimer (0.030 mol) and 0.050 g of (S,S)-f-Binaphane (0.063 mmol) were dissolved in 50 mL of toluene. The reaction mixture was allowed to stand for 15 min, added with 50 mL of the degassed toluene containing 1.150 g of dimethyl 4-(4,9-dihydro-3H-pyrido[3,4-b]indol-1-yl)-4-ethylpimelate (IIa) (3.000 mmol) and 0.050 g of potassium iodide (0.300 mmol) and then transferred to a high-pressure reactor. The high-pressure reactor was subjected to hydrogen substitution three times and then introduced with hydrogen to 60 atm. The reaction mixture was stirred at −20° C. for 100 h, and then the hydrogen was slowly discharged. The reaction mixture was evaporated to remove the solvent and separated by a silica gel column to give 1.009 g of a white powder product (Ia) (95% yield, dr(cis/trans)=1:5, cis: 94% ee and greater than 99% after recrystallization, trans: 94% ee and greater than 99% after recrystallization).

$^1$H NMR (600 MHz, $CCl_3$-d) δ8.05 (s, 1H), 7.51 (d, J=5.2 Hz, 1H), 7.36 (d, J=5.2 Hz, 1H), 7.19 (t, J=5.2 Hz, 1H), 7.13 (t, J=5.2 Hz, 1H), 5.20-5.10 (m, 1H), 4.83 (s, 1H), 3.57 (s, 3H), 2.88-2.70 (m, 3H), 2.60-2.42 (m, 2H), 2.16-2.12 (m, 2H), 2.00-1.86 (m, 2H), 1.80-1.74 (m, 2H), 1.59-1.55 (m, 1H), 1.49-1.39 (m, 1H), 1.17 (t, J=5.2 Hz, 3H) ppm.

HRMS (ESI) m/z $C_{21}H_{26}NaN_2O_3$ [M+Na]$^+$ (calculated: 377.1836; measured: 377.1838).

Example 2 Preparation of isopropyl 3-[(1S,12bS)-1-ethyl-1,2,3,4,6,7,12,12b-octahydro-4-oxoindolo[2,3-a]quinolizin-1-yl]propionate (Ia)

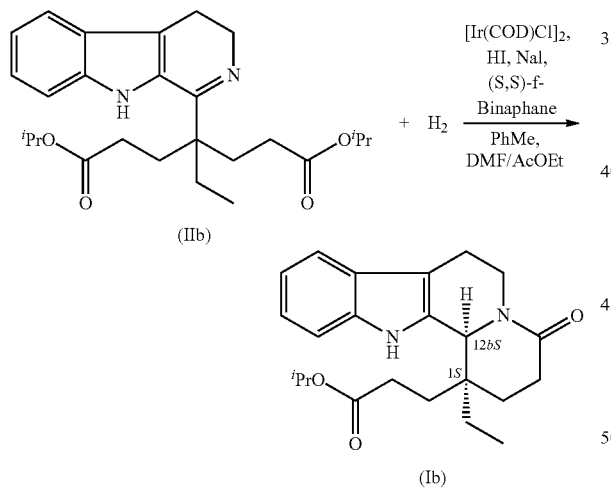

Under an argon atmosphere, 0.008 g of chloro(1,5-cyclooctadiene)iridium(I) dimer (0.012 mol) and 0.021 g of (S,S)-f-Binaphane (0.026 mmol) were dissolved in 2 mL of toluene, to which 0.013 mL of a 5.3 mmol/mL aqueous hydrogen iodide solution was added via a pipette. The reaction mixture was stirred at room temperature for 10 h and concentrated to remove the solvent. The resulting product was dissolved with 0.5 mL of dichloromethane, to which 0.5 mL of n-hexane was added. The reaction mixture was filtered under vacuum, and the filter residue was dried and dissolved in 24 mL of a degassed mixture of N,N-dimethylformamide and ethyl acetate (v/v=1:1), to which 0.211 g of diisopropyl 4-(4,9-dihydro-3H-pyrido[3,4-b]indol-1-yl)-4-ethylpimelate (IIb) (0.480 mmol) and 0.007 g of sodium iodide (0.148 mmol) were then added in one time. The reaction mixture was transferred to a high-pressure reactor, and then the high-pressure reactor was subjected to hydrogen substitution three times and introduced with hydrogen to 60 bar. The reaction mixture was stirred at −20° C. for 150 h. After the hydrogen was completely discharged, the reaction mixture was evaporated to remove the solvent and separated by a silica gel column to give 0.165 g of a white foamy product (Ib) (90% yield, dr(cis/trans)=1.9:1, cis: 89% ee, trans: 88% ee) with [α]$^{25}_D$ of −90.2 (c0.3, $CH_2Cl_2$).

$^1$H NMR (400 MHz, $CCl_3$-d) δ8.13 (s, 1H), 7.51 (d, J=7.6 Hz, 1H), 7.36 (d, J=8.0 Hz, 1H), 7.22-7.07 (m, 2H), 5.18-5.10 (m, 1H), 4.94-4.86 (m, 1H), 4.81 (s, 1H), 2.91-2.69 (m, 3H), 2.59-2.43 (m, 2H), 2.20-2.06 (m, 2H), 1.98-1.84 (m, 2H), 1.83-1.69 (m, 2H), 1.62-1.52 (m, 1H), 1.50-1.42 (m, 1H), 1.18-1.14 (m, 9H) ppm.

HRMS (ESI) $C_{23}H_{30}NaN_2O_3$ [M+Na]$^+$ m/z (calculated: 405.2149; measured: 405.2147).

Example 3 Preparation of methyl 3-[(1S,12bS)-1-ethylmethylether-1,2,3,4,6,7,12,12b-octahydro-4-oxoindolo[2,3-a]quinolizin-1-yl] propionate (Ic)

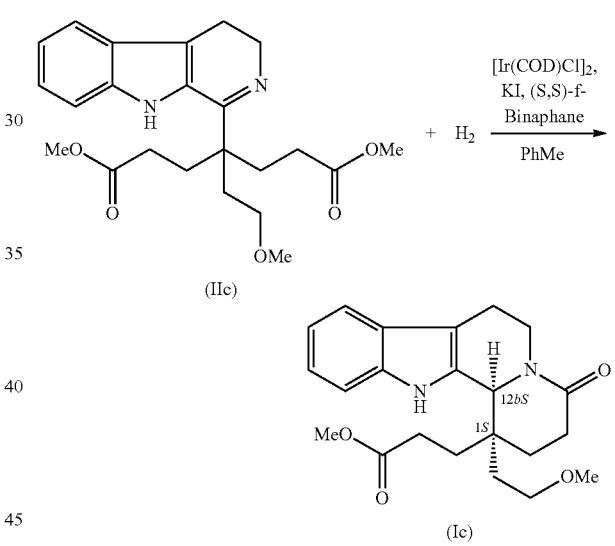

In a dry flask, 0.002 g of chloro(1,5-cyclooctadiene)iridium(I) dimer (0.003 mol) and 0.005 g of (S,S)-f-Binaphane (0.006 mmol) were dissolved in 2 mL of degassed toluene. The reaction mixture was allowed to stand for 15 min, added with 3 mL of degassed toluene containing 0.040 g of dimethyl 4-(4,9-dihydro-3H-pyrido[3,4-b]indol-1-yl)-4-ethylmethylether pimelate (IIc) and 0.002 g of potassium iodide (0.010 mmol) and transferred to a high-pressure reactor. The high-pressure reactor was subjected to hydrogen substitution three times and introduced with hydrogen to 60 atm. The reaction mixture was stirred at −20° C. for 120 h, and then the hydrogen was slowly discharged. The reaction mixture was evaporated to remove the solvent and separated by a silica gel column to give 0.033 g of a white foamy product (85% yield, dr(cis/trans)=4.2:1, cis: 90% ee, trans: 89% ee).

$^1$H NMR (400 MHz, $CCl_3$-d) δ9.42 (s, 1H), 7.51 (d, J=6.8 Hz, 1H), 7.36 (d, J=8.0 Hz, 1H), 7.21-7.14 (td, J=6.8, 1.2 Hz, 1H), 7.10 (td, J=8.0, 1.2 Hz, 1H), 5.18-5.09 (m, 1H), 5.03 (s, 1H), 3.80-3.70 (m, 2H), 3.56 (s, 3H), 3.45 (s, 3H), 2.81-2.67

(m, 3H), 2.65-2.45 (m, 2H), 2.36-2.29 (m, 1H), 2.14-2.00 (m, 3H), 1.83-1.75 (m, 1H), 1.72-1.62 (m, 1H), 1.55-1.48 (m, 1H), 1.35-1.27 (m, 1H) ppm.

HRMS (ESI) m/z $C_{22}H_{28}NaN_2O_4$ [M+Na]$^+$ (calculated: 407.1941; measured: 407.1945).

Example 4 Preparation of methyl 3-[(1S,12bS)-1-ethyl tert-butyl ether-1,2,3,4,6,7,12,12b-octahydro-4-oxoindolo[2,3-a]quinolizin-1-yl] propionate (Id)

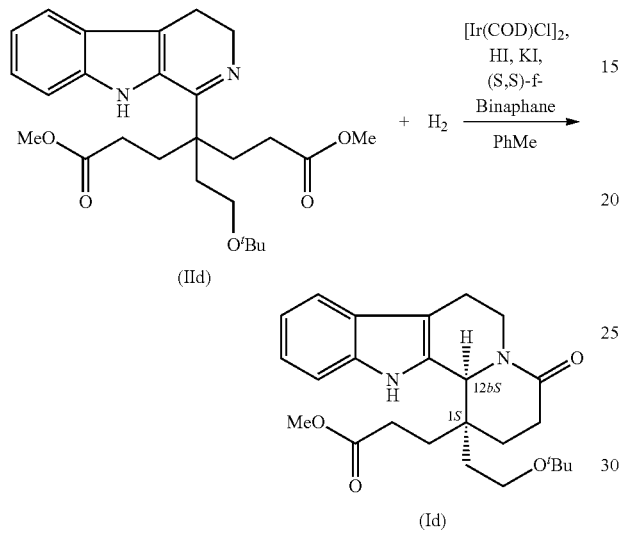

Under an argon atmosphere, 0.008 g of chloro(1,5-cyclooctadiene)iridium(I) dimer (0.012 mol) and 0.021 g of (S,S)-f-Binaphane (0.026 mmol) were dissolved in 2 mL of toluene, to which 0.013 mL of a 5.3 mmol/mL aqueous solution of hydrogen iodide was added via a pipette. The reaction mixture was stirred at room temperature for 10 h and concentrated to remove the solvent. The resulting product was dissolved with 0.5 mL of dichloromethane, to which 0.5 mL of n-hexane was added. The reaction mixture was filtered under vacuum, and the filter residue was dried and dissolved in 22 mL of degassed toluene, to which 0.228 g of dimethyl 4-(4,9-dihydro-3H-pyrido[3,4-b]indol-1-yl)-4-ethyl tert-butyl ether pimelate (IId) (0.500 mmol) and 0.025 g of sodium iodide (0.150 mmol) were then added in one time. The reaction mixture was transferred to a high-pressure reactor, and then the high-pressure reactor was subjected to hydrogen substitution three times and introduced with hydrogen to 60 atm. The reaction mixture was stirred at −20° C. for 150 h. After the hydrogen was completely discharged, the reaction mixture was evaporated to remove the solvent and separated by a silica gel column to give 0.206 g of a yellow powder product (Id) (92% yield, dr(cis/trans)=17:1, cis: 88% ee and greater than 99% after recrystallization, trans: 78% ee) with $[\alpha]^{25}D$ of −79.5 (c1.0, $CH_2Cl_2$).

$^1$H NMR (400 MHz, $CCl_3$-d) δ10.04 (s, 1H), 7.52 (d, J=7.6 Hz, 1H), 7.32 (d, J=8.0 Hz, 1H), 7.21-7.13 (t, J=8.0 Hz, 1H), 7.10 (t, J=7.6 Hz, 1H), 5.20-5.10 (m, 1H), 5.07 (s, 1H), 3.87-3.64 (m, 2H), 3.56 (s, 3H), 2.85-2.66 (m, 3H), 2.62-2.48 (m, 2H), 2.28-2.21 (m, 1H), 2.14-1.96 (m, 3H), 1.87-1.66 (m, 2H), 1.55-1.49 (m, 1H), 1.37-1.26 (m, 10H) ppm.

HRMS (ESI) m/z $C_{25}H_{34}NaN_2O_4$ [M+Na]$^+$ (calculated: 449.2411; measured: 449.2411).

Described above are merely preferred embodiments of the invention, and the invention is not limited thereto. Various modifications, changes and replacements made by those skilled in the art without departing from the spirit of the invention should fall within the scope defined by the appended claims.

What is claimed is:

1. A method of synthesizing a (1S,12bS) lactam ester compound of formula (I)

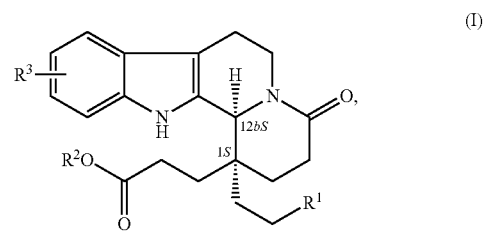

comprising:
subjecting a dihydrocarboline diester compound of formula (II) to asymmetric hydrogenation and lactamization in an organic solvent in the presence of chloro(1,5-cyclooctadiene)iridium(I) dimer, (S,S)-f-Binaphane and a halogen-containing reagent under hydrogen atmosphere to produce the (1S,12bS) lactam ester compound (I), as shown in the following reaction scheme:

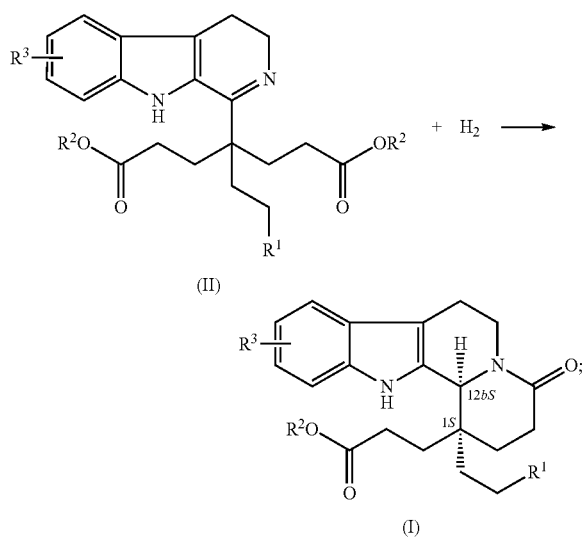

wherein:
R$^1$ is hydrogen, linear $C_1$-$C_5$ alkyl ether group, branched $C_1$-$C_5$ alkyl ether group, allyl ether group, benzyl ether group, methyl silyl ether group, isopropyl silyl ether group, tert-butyl silyl ether group or phenylsilyl ether group;
R$^2$ is linear or branched $C_1$-$C_5$ alkyl, aralkyl or aryl; and
R$^3$ is hydrogen, linear or branched $C_1$-$C_5$ alkyl, linear or branched $C_1$-$C_3$ alkoxy or halogen.

2. The method of claim 1, wherein R$^1$ is hydrogen or linear or branched $C_1$-$C_5$ alkyl ether group;
R$^2$ is linear or branched $C_1$-$C_5$ alkyl; and
R$^3$ is hydrogen or linear or branched $C_1$-$C_5$ alkyl.

3. The method of claim 1, wherein the halogen-containing reagent is halogen, an aqueous solution of hydrogen halide, a halide salt or a combination thereof; wherein the halogen is bromine or iodine; the aqueous solution of hydrogen halide is an aqueous solution of hydrogen iodide or hydrogen bromide; and the halide salt is potassium bromide, potassium iodide, sodium bromide or sodium iodide.

4. The method of claim 1, wherein a molar ratio of the dihydrocarboline diester compound of formula (II) to the chloro(1,5-cyclooctadiene)iridium(I) dimer to the (S,S)-f-Binaphane to halogen anions in the halogen-containing reagent is 1:0.01-0.05:0.02-0.1:0.1-0.5.

5. The method of claim 1, wherein in the asymmetric hydrogenation and lactamization, a hydrogen pressure is 20-100 atm, a reaction temperature is −40° C.-40° C., and a reaction time is 48-200 h.

6. The method of claim 1, wherein the organic solvent is a single or mixed polar aprotic organic solvent, or an apolar aprotic organic solvent.

7. The method of claim 1, wherein the halogen-containing reagent is a single halogen-containing reagent, and the method comprises:
   (1) dispersing the chloro(1,5-cyclooctadiene)iridium(I) dimer and the (S,S)-f-Binaphane in a part of the organic solvent; and subjecting the reaction mixture to standing or stirring at room temperature for 10-30 min;
   (2) adding dihydrocarboline diester compound of formula (II), the halogen-containing reagent and the rest of the organic solvent to the reaction mixture obtained in step (1); and
   (3) transferring the reaction mixture obtained in step (2) to a high-pressure reactor; and subjecting the reaction mixture to the asymmetric hydrogenation and lactamization under hydrogen atmosphere.

8. The method of claim 2, wherein the halogen-containing reagent is a single halogen-containing reagent, and the method comprises:
   (1) dispersing the chloro(1,5-cyclooctadiene)iridium(I) dimer and the (S,S)-f-Binaphane in a part of the organic solvent; and subjecting the reaction mixture to standing or stirring at room temperature for 10-30 min;
   (2) adding dihydrocarboline diester compound of formula (II), the halogen-containing reagent and the rest of the organic solvent to the reaction mixture obtained in step (1); and
   (3) transferring the reaction mixture obtained in step (2) to a high-pressure reactor; and subjecting the reaction mixture to the asymmetric hydrogenation and lactamization under hydrogen atmosphere.

9. The method of claim 1, wherein the halogen-containing reagent is a combination of a first halogen-containing reagent and a second halogen-containing reagent, and the method comprises:
   (1) dispersing the chloro(1,5-cyclooctadiene)iridium(I) dimer and the (S,S)-f-Binaphane in the organic solvent under an inert gas; adding the first halogen-containing reagent; and reacting the reaction mixture at room temperature under stirring for 5-20 h to produce a halogen-bridged iridium complex solution;
   (2) subjecting the halogen-bridged iridium complex solution obtained in step (1) to separation and purification; and drying the purified product;
   (3) dissolving the dried product obtained in step (2) in an organic solvent which is the same as or different from the organic solvent used in step (1); and adding the dihydrocarboline diester compound of formula (II) and the second halogen-containing reagent to the reaction mixture; and
   (4) transferring the reaction mixture to a high-pressure reactor; and subjecting the reaction mixture to the asymmetric hydrogenation and lactamization under hydrogen atmosphere;
   wherein a molar ratio of halogen anions in the first halogen-containing reagent to halogen anions in the second halogen-containing reagent is 0.2-2:1.

10. The method of claim 2, wherein the halogen-containing reagent is a combination of a first halogen-containing reagent and a second halogen-containing reagent, and the method comprises:
   (1) dispersing the chloro(1,5-cyclooctadiene)iridium(I) dimer and the (S,S)-f-Binaphane in the organic solvent under an inert gas; adding the first halogen-containing reagent; and reacting the reaction mixture at room temperature under stirring for 5-20 h to produce a halogen-bridged iridium complex solution;
   (2) subjecting the halogen-bridged iridium complex solution obtained in step (1) to separation and purification; and drying the purified product;
   (3) dissolving the dried product obtained in step (2) in an organic solvent which is the same as or different from the organic solvent used in step (1); and adding the dihydrocarboline diester compound of formula (II) and the second halogen-containing reagent to the reaction mixture; and
   (4) transferring the reaction mixture to a high-pressure reactor; and subjecting the reaction mixture to the asymmetric hydrogenation and lactamization under hydrogen atmosphere;
   wherein a molar ratio of halogen anions in the first halogen-containing reagent to halogen anions in the second halogen-containing reagent is 0.2-2:1.

* * * * *